United States Patent
Goldberg et al.

(10) Patent No.: US 11,938,228 B2
(45) Date of Patent: *Mar. 26, 2024

(54) PARTICLE-BASED MULTI-LAYER THERAPEUTIC DELIVERY DEVICE AND METHOD

(71) Applicant: Privo Technologies, Inc., Peabody, MA (US)

(72) Inventors: Manijeh Nazari Goldberg, Newburyport, MA (US); Brandon LaPorte, Methuen, MA (US); Aaron Manzi, Atkinson, NH (US); Amritpreet Birdi, Peabody, MA (US)

(73) Assignee: PRIVO TECHNOLOGIES, INC., Peabody, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/241,408

(22) Filed: Jan. 7, 2019

(65) Prior Publication Data

US 2019/0142760 A1    May 16, 2019

Related U.S. Application Data

(62) Division of application No. 15/932,315, filed on Feb. 16, 2018, now abandoned.

(60) Provisional application No. 62/460,665, filed on Feb. 17, 2017.

(51) Int. Cl.
```
A61K 9/70      (2006.01)
A61K 9/00      (2006.01)
A61K 9/107     (2006.01)
A61K 9/16      (2006.01)
A61K 9/20      (2006.01)
A61K 9/24      (2006.01)
A61K 31/616    (2006.01)
A61K 47/02     (2006.01)
A61K 47/36     (2006.01)
A61K 47/38     (2006.01)
```

(52) U.S. Cl.
CPC .......... *A61K 9/70* (2013.01); *A61K 9/0014* (2013.01); *A61K 9/006* (2013.01); *A61K 9/107* (2013.01); *A61K 9/167* (2013.01); *A61K 9/2077* (2013.01); *A61K 9/2086* (2013.01); *A61K 9/209* (2013.01); *A61K 31/616* (2013.01); *A61K 47/02* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 3,983,173 A * | 9/1976 | Hartung | C07D 405/04 544/154 |
| 4,638,043 A * | 1/1987 | Szycher | A61L 15/26 522/6 |
| 4,765,983 A * | 8/1988 | Takayanagi | A61P 25/04 424/435 |
| 4,895,724 A | 1/1990 | Cardinal et al. | |
| 4,997,425 A * | 3/1991 | Shioya | A61F 13/00063 604/378 |
| 5,447,940 A * | 9/1995 | Harvey | A61K 9/0063 424/435 |
| 6,071,528 A * | 6/2000 | Jensen | A61K 6/76 424/407 |
| 10,159,651 B2 | 12/2018 | Goldberg et al. | |
| 10,398,655 B2 | 9/2019 | Goldberg et al. | |
| 10,478,403 B1 | 11/2019 | Goldberg et al. | |
| 2003/0017195 A1 | 1/2003 | Mitragotri et al. | |
| 2003/0049208 A1 * | 3/2003 | Ream | A61K 9/0058 424/48 |
| 2004/0106344 A1 | 6/2004 | Looney | |
| 2004/0151774 A1 | 8/2004 | Pauletti | |
| 2005/0013866 A1 | 1/2005 | Maincent et al. | |

(Continued)

FOREIGN PATENT DOCUMENTS

AU    2014218717 B2    8/2014
DE    10213427 A1    10/2003

(Continued)

OTHER PUBLICATIONS

Mohandas et al. Journal of Materials Chemistry B 2015 3:5795 (Year: 2015).*

(Continued)

*Primary Examiner* — Melissa S Mercier
*Assistant Examiner* — Caralynne E Helm
(74) *Attorney, Agent, or Firm* — Mintz Levin Cohn Ferris Glovsky and Popeo, P.C.

(57) ABSTRACT

A device for delivery of a first therapeutic agent and a second therapeutic agent to a site in epithelial tissue includes a first layer having a first, freeze-dried polymeric matrix having first and second opposed surfaces, formed by a composition including chitosan, a hydration promoter, a particle adhesion inhibitor, and a particle aggregation inhibitor, and a plurality of first particles embedded within the first matrix so as to be directly surrounded by, and in contact with, the first matrix, the first particles containing the first therapeutic agent and having a coating around the first therapeutic agent, the coating including chitosan. The device further includes a second layer, adjacent to the first layer, having a second, freeze-dried polymeric matrix containing the second therapeutic agent, the first layer and/or the second layer is configured to be attached to the site in the epithelial tissue.

7 Claims, 7 Drawing Sheets

(56) References Cited

U.S. PATENT DOCUMENTS

| | | | |
|---|---|---|---|
| 2005/0137512 A1 | 6/2005 | Campbell | |
| 2005/0147656 A1 | 7/2005 | McCarthy | |
| 2006/0210604 A1 | 9/2006 | Dadey et al. | |
| 2007/0254016 A1* | 11/2007 | Andersen | A61K 9/122 424/443 |
| 2008/0044478 A1 | 2/2008 | Ramstack et al. | |
| 2008/0220030 A1 | 9/2008 | Fernandez et al. | |
| 2009/0018479 A1 | 1/2009 | McCarthy | |
| 2009/0280182 A1* | 11/2009 | Beck | A61L 15/225 424/486 |
| 2009/0299328 A1 | 12/2009 | Mudd et al. | |
| 2010/0003300 A1 | 1/2010 | Markland et al. | |
| 2010/0112050 A1* | 5/2010 | Ryoo | A61K 9/2018 514/777 |
| 2010/0135979 A1 | 6/2010 | Jederstrom | |
| 2010/0167401 A1 | 7/2010 | Hasirci | |
| 2011/0044911 A1 | 2/2011 | Akhtari et al. | |
| 2011/0111011 A1 | 5/2011 | Giovinazzo et al. | |
| 2011/0287110 A1 | 11/2011 | Dewhirst et al. | |
| 2012/0009260 A1 | 1/2012 | Schobel et al. | |
| 2012/0071567 A1* | 3/2012 | Crowley | A23G 3/46 426/654 |
| 2013/0273138 A1 | 10/2013 | Serizawa | |
| 2014/0046236 A1* | 2/2014 | Filee | A61L 15/425 602/43 |
| 2014/0081070 A1 | 3/2014 | Paukshto | |
| 2014/0234212 A1 | 8/2014 | Goldberg et al. | |
| 2015/0174076 A1* | 6/2015 | Harris | A61K 31/352 424/489 |
| 2017/0329189 A1 | 11/2017 | Kim et al. | |
| 2018/0154001 A1 | 6/2018 | Dadey et al. | |
| 2018/0169025 A1 | 6/2018 | Goldberg et al. | |
| 2018/0235899 A1 | 8/2018 | Goldberg et al. | |
| 2019/0298799 A1 | 10/2019 | Lichter et al. | |
| 2019/0388356 A1 | 12/2019 | Goldberg et al. | |
| 2020/0078315 A1 | 3/2020 | Goldberg et al. | |
| 2020/0108072 A1 | 4/2020 | Honigberg et al. | |
| 2020/0306264 A1 | 10/2020 | Surber | |
| 2021/0087198 A1 | 3/2021 | Rennie et al. | |
| 2022/0387340 A1 | 12/2022 | Goldberg et al. | |
| 2023/0103552 A1 | 4/2023 | Goldberg et al. | |

FOREIGN PATENT DOCUMENTS

| | | |
|---|---|---|
| DE | 10313427 A1 | 1/2004 |
| EP | 562864 A1 * | 9/1993 |
| EP | 1348830 A2 | 10/2003 |
| JP | 63090507 A | 4/1988 |
| KR | 200340228 Y1 | 1/2004 |
| WO | WO 2005/023323 A1 | 3/2005 |
| WO | WO 2014/130866 A2 | 8/2014 |
| WO | 2017143294 A1 | 8/2017 |
| WO | 2021138646 A1 | 7/2021 |
| WO | 2022256417 A1 | 12/2022 |

OTHER PUBLICATIONS

Maya et al. International Journal of Biological Macromolecules 2012 51:392-399 (Year: 2012).*
Mi et al. Journal of Biomedical Material Research 2002 59:438-449 (Year: 2002).*
Rodriguez-Arguelles et al. Journal of Colloid and Interfacial Science 2011 364:80-84 (Year: 2011).*
Cacciotti et al. Carbohydrate Polymers 2014 103:22-31 (Year: 2014).*
Lee et al. International Journal of Nanomedicine 2016 11:285-297 (Year: 2016).*
Hwang et al. AAPS PharmSciTech 2010 11(3):1092-1103 (Year: 2010).*
Ibrahim et al. Journal of Applied Pharmaceutical Science 2015 5 (10):085-090 (Year: 2015).*
Li et al. Dental Materials 2014 30:172-181 (Year: 2014).*
Lee et al. Artificial Organs 2004 28(9):829-839 (Year: 2004).*
DeFail et al. Biomaterials 2006 27:1579-1585 (Year: 2006).*
Ji et al. Carbohydrate Polymers 2011 85:803-808 (Year: 2011).*
Jonassen et al. Biomacromolecules 2012 13:3747-3756 (Year: 2012).*
Amasya et al. Turkish Journal of Pharmaceutical Sciences 2012 9(1):1-12 (Year: 2012).*
Barat et al. Acta Pharmaceutica 2007 57:469-477 (Year: 2007).*
American Cancer Society, "What is Melanoma Skin Cancer?," 5 pages, retrieved from the internet on Apr. 6, 2017 [http://www.cancer.org/cancer/skincancer-melanoma/detailedguide/melanoma-skincancer-what-is-melanoma].
American Cancer Society, "Causes, Risk Factors, and Prevention," Colorectal Cancer detailed guide, 17 pages, retrieved from the Internet on Mar. 8, 2017 [https://www.cancer.org/cancer/colon-rectal-cancer.html].
American Cancer Society, "Understanding Advanced Cancer, Metastatic Cancer, and Bone Metastasis," American Cancer Society, 8 pages, retrieved from the internet on Jul. 23, 2018 [http://www.cancer.org/treatment/understanding-your diagnosis/advanced-cancer/what-is . . . ].
Barker N., et al., "The intestinal stem cell," Genes & Dev., vol. 22, pp. 1856-1864 (2008).
Bhandari, B., et al. (Editors)., "Nutrient Digestion and Absorption in the Gastrointestinal Tract," Food Materials Science and Engineering, Section 8.2, 2 pages (Aug. 2012).
Cancer Treatment Centers of America, "Hyperthermic intraperitoneal chemotherapy (HIPEC)", 2 pages, retrieved from the internet on Jul. 20, 2018.
Children's Hospital of Pittsburgh of UPMC, "Enema Administration," 2 pages, retrieved from the internet on Mar. 7, 2017 [http://www.chp.edu/our-services/surgery-pediatric/pediatric-surgery-services-we-offer/colorectal-center-for-children/patient-family-resources/enema-adminstration].
Dai T., et al., "Chitosan preparations for wounds and burns: antimicrobial and wound-healing effects," Expert Rev. Anti. Infect. Therapy, vol. 9, No. 7, pp. 857-879 (Jul. 2011).
Dillekås H, et al., "Differences in metastatic patterns in relation to time between primary surgery and first relapse from breast cancer suggest synchronized growth of dormant micrometastases," Breast Cancer Res. Treat., vol. 146, No. 3, pp. 627-636 (2014).
Familydoctor.org., "Burning: Preventing Burns in Your Home," 3 pages, retrieved from the Internet on Apr. 6, 2017 [https://familydoctor.org/burns-preventing-burns-in-your-home/].
Fightcolorectalcancer.org, "Managing Side Effects," 7 pages, retrieved from the internet on Mar. 7, 2017.
Gillenwater A., et al., "Oral Premalignancy: New Methods of Detection and Treatment," Curr. Oncol. Rep., vol. 8, No. 2, pp. 146-154 (Mar. 2006).
Gisbert J. P., et al., "Inflammatory Bowel Disease in the Elderly," Ailment Pharmacol. Ther., vol. 39, No. 5, pp. 459-477 (2014).
Glynne-Jones, R., et al., "Anal cancer: ESMO Clinical Practice Guidelines for diagnosis, treatment and follow-up," Annals of Oncology, vol. 21, Suppl. 5, pp. v87-v92 (2010).
Gupta K.C., et al., "Drug release behavior of beads and microgranules of chitosan," Biomaterials, vol. 21, Issue 11, pp. 1115-1119 (Jun. 2000).
Hall D., "The Three Phases of the Foo Digestion Process," LIVESTRONG.com, 14 pages, retrieved from the Internet on Mar. 7, 2017 [http://www.livestrong.com/article/312184-the-three-phases-of-the-food-digestion-process/].
Harless W.W., et al., "Revisiting perioperative chemotherapy: the critical importance of targeting residual cancer prior to wound healing," BMC Cancer, vol. 9, No. 118, 9 pages (Apr. 2009).
Hanauer S.B., et al., "Budesonide Enema for the Treatment of Active, Distal Ulcerative Colitis and Proctitis: A Dose-Ranging Study," Gastroenterology, vol. 115, No. 3, pp. 525-532 (Sep. 1998).
Henderson R., "Prescribing for Children," Patient Platform Limited, 3 pages, retrieved from the Internet on Mar. 7, 2017 [http://patient.info/doctor/prescribing-for-children].
Hookman P., et al., "Clostridium Difficile associated infection, diarrhea and colitis," World Journal of Gastroenterology, vol. 15, No. 13, pp. 1554-1580 (Apr. 2009).

(56) References Cited

OTHER PUBLICATIONS

Jacobson J.J., et al., "The cost burden of oral, oral pharyngeal, and salivary gland cancers in three groups: commercial insurance, medicare, and medicaid," *Head and Neck Oncology*, vol. 4, No. 15, 17 pages (2012).

Khan A., et al., "Burns: Types, Treatments, and More," *Healthline Newsletters*, 15 pages, retrieved from the internet on Apr. 5, 2017 [http://www.healthline.com/health/burns?m=0#Overview1].

Koh P.K., et al., "A Systematic review of the function and complications of colonic pouches," *Int. J. Colorectal Dis.*, vol. 22, pp. 543-548 (2007).

Kulkarnia A.R., et al., "In-vitro release kinetics of cefadroxil-loaded sodium alginate interpenetrating network beads," *European Journal of Pharmaceutics and Biopharmaceutics*, vol. 51, No. 2, pp. 127-133 (Mar 2001).

Lai S.K., et al., "Mucus-penetrating nanoparticles for drug and gene delivery to mucosal tissues," *Adv. Drug Deliv. Rev.*, vol. 61, No. 2, pp. 158-171 (Feb. 2009).

Laksitorini M., et al., "Pathways and Progress in Improving Drug Delivery Through the Intestinal Mucosa and Blood-Brain Barriers," *Ther. Deliv.*, vol. 5, No. 10, pp. 1143-1163 (Oct. 2014).

Liu Z., et al., "Polysaccharides-based nanoparticles as drug delivery systems," *Adv. Drug Deliv. Rev.*, vol. 60, No. 15, pp. 1650-1662 (Dec. 2008).

Macrae F.A., et al., "Clinical presentation, diagnosis, and staging of colorectal cancer," *UpToDate*, 20 pages, retrieved from the Internet on Mar. 8, 2017 [http://www.uptodate.com/contents/clinical-presentation-diagnosis-and-staging-of-colorectal-cancer].

Makarios-Laham I., et al., "Biodegradability of Chitin—and Chitosan-Containing Films in Soil Environment," *Journal of Environmental Polymer Degradation*, vol. 3 No. 1, pp. 31-16 (Jan. 1995).

MDconsult.com., "Anatomy and Histology of the Small and Large Intestine," 18 pages, retrieved from the Internet on Mar. 8, 2017 [http://jpck.zju.edu.cn/jcyxjp/filed/ge/05/MT/0511.pdf].

Misono S., et al., "Incidence of Suicide in Persons With Cancer," *Journal of Clinical Oncology*, vol. 26, No. 29, pp. 4731-4738 (Oct. 10, 2008).

Mulcahy M., "When Fighting Cancer Isn't Worth It," *The Atlantic—Health*, 5 pages (Dec. 2012).

Murata Y., et al., "Use of floating alginate gel beads for stomach-specific drug delivery," *Eur. J. Pharm. Biopharm.*, vol. 50, Issue 2, pp. 221-226 (Sep. 2000).

Nagpal K., et al., "Chitosan Nanoparticles: A Promising System in Novel Drug Delivery," *Chemical and Pharmaceutical Bulletin*, vol. 58, No. 11, pp. 1423-1430 (Nov. 2010).

National Cancer Institute, "Surveillance, Epidemiology, and End Result Program (SEER)," —Cancer of the Colon and Rectum—Cancer Stat Facts, 9 pages. retrieved from the internet on Mar. 7, 2017.

National Cancer Institute, "Surveillance, Epidemiology, and End Result program (SEER)," Cancer of the Anus, Anal Canal, and Anorectum—Cancer Stat Facts, 9 pages, retrieved from the internet on Mar. 15, 2017 [https://seer.cancer.gov/statfacts/html/colorect.html].

National Cancer Institute, "Metastatic Cancer, What is Metastatic Cancer?," 5 pages, retrieved from internet on Jul. 20, 2018.

National Psoriasis Foundation, "50 Years Driving Discovery, Creating Community," National Psoriasis Foundation, 4 pages, retrieved from the internet on Apr. 6, 2017.

National Psoriasis Foundation, "Causes and Triggers," 6 pages, retrieved from the internet on Apr. 6, 2017 [https://www.psoriasis.org/about-psoriasis/causes].

New Radiant Technology S.p.A., "Novac 7, The first mobile elecron linear accelerator for IORT", 6 pages, retrieved from the internet on Jul. 20, 2018 [http://sennewald.de/wp-content/uploads/novac7.pdf].

Patil P., et al., "A Review on Ionotropic Gelation Method: Novel Approach for Controlled Gastroretentive Gelispheres," *Int. J. Pharm. Pharm. Sci.* vol. 4, Suppl. 4, pp. 27-32 (2012).

Paun B.C., et al., "Postoperative Complications Following Surgery for Rectal Cancer," *Annals of Surgery*, vol. 251, No, 5, pp. 807-818 (2010).

Ryan D.P., et al., "Clinical features, staging, and treatment of anal cancer," 10 pages, retrieved from the internet on Mar. 8, 2017 [http://www.uptodate.com/contents/clinical-features-staging-and-treatment-of-anal-cancer].

Saramento B., et al., "Chitosan-Based Systems for Biopharmaceuticals: Delivery, Targeting and Polymer Therapeutics," *John Wiley & Son, Ltd.*, 564 pages (Mar. 2012).

Shaw D et al., "Intestinal mucosal atrophy and adaptation," *World Journal of Gastroenterology*, vol. 18, Issue 44, pp. 6357-6375 (Nov. 2012).

Sperk et al., "A cohort analysis to identify eligible patients for intraoperative radiotherapy (IORT) of early breast cancer" *Radiation Oncology*, vol. 9, No. 154, 7 pages (2014).

The HPV and Anal Cancer Foundation, "Living with Anal Cancer/Causes & Risk Factors," 8 pages, retrieved from the internet on Mar. 7, 2017 [http://www.analcancerfoundation.org/living-with-anal-cancer/anal-cancer-risk-factors-causes/].

The HPV and Anal Cancer Foundation, "Living With Anal Cancer/Treatment for Anal Cancer," 18 pages, retrieved from the internet on Mar. 8, 2017 [http://www.analcancerfoundation.org/living-with-anal-cancer/anal-cancer-treatment/].

The Oral Cancer Foundation, The Oral Cancer Foundation website, 3 pages, retrieved from the internet on Mar. 9, 2017 [http://oralcancerfoundation.org/].

The Oral Cancer Foundation, "Mucositis," 14 pages, retrieved from the internet on Mar. 9, 2017 [http://oralcancerfoundation.org/complications/mucositis].

Tufts Medical Center, "Cytoreductive Surgery with Hyperthermic Intraperitoneal Chemotherapy (HIPEC)," HIPEC FAQ's, 2 pages, retrieved from the internet on Jul. 20, 2018.

Tufts Medical Center, "Cytoreductive Surgery with Hyperthermic Intraperitoneal Chemotherapy (HIPEC)" 7 pages, retrieved from the internet on Jul. 20, 2018.

Tulunay O. et al., "Pilot Study of Intraoperative Chemotherapy with Cisplatin and 5-Fluorouracil in Patients with Advanced Squamous Cell Carcinoma of the Head and Nec," *Head & Neck*, vol. 29, Issue 3, pp. 267-271 (Mar. 2007).

Weinberg M.A. et al., "Assessing Oral Malignancies," *American Family Physician*, vol. 65, No. 7, pp. 1379-1384 (Apr. 2002).

West Virginia University, "Intraoperative Radiation Therapy," WVU Medicine Health Report, 3 pages, retrieved from the internet on Jul. 20, 2018 [https://www.cancercenter.com/treatments/intraoperative-radiation-therapy/].

Willett, C.G. et al., "Adjuvant therapy for resected rectal adenocarcinoma," 5 pages, retrieved from the Internet on Mar. 8, 2017 [http://www.uptodate.com/contents/adjuvant-therapy-for-resected-rectal-adenocarcinoma].

Youssef N.N, et al., "Management of Intractable Constipation With Antegrade Enemas in Neurologically Intact Children," *Journal of Pediatric Gastroenterology & Nutrition*, vol. 34, No. 4, pp. 402-405 (Apr. 2002).

Zhang H et al., "Effect of chitosan and carboxymethyl chitosan on fibrinogen structure and blood coagulation." *J. Biomater. Sci. Polym. Ed.*, vol. 24, No. 13, pp. 1549-1563 (2013).

Zhang Z et al., "Polymeric nanoparticles-based topical delivery systems for the treatment of dermatological diseases," *Nanomdicine and Nanobiotechnology*, vol. 5, Issue 3, pp. 205-218 (May/Jun. 2013).

Zhang Z et al., "Effect of chitosan and carboxymethyl chitosan on fibrinogen structure and blood coagulation." *J. Biomater. Sci. Polym. Ed.*, vol. 24, No. 13, pp. 1549-1563 (2013).

M. Vázques, Lantes, *Authorized officer*, International Search Report—Application No. PCT/US2014/017790, 4 pages (dated May 19, 2014).

International Search Report—Application No. PCT/US2018/000065, 6 pages (dated May 28, 2018).

M. Vázquez, Lantes, *Authorized Officer* Written Opinion of the International Searching Authority—Application No. PCT/US2017/018514, 7 pages (dated Jul. 3, 2017).

(56) References Cited

OTHER PUBLICATIONS

Bruce D. Sunstein, Esq. Sunstein Kann Murphy & Timbers LLP, Supplement to Response C—U.S. Appl. No. 15/436,651, 12 pages (filed on Jun. 22, 2018).
Kortney L. Klinkel, Primary Examiner United States Patent and Trademark Office, Non-Final Action—U.S. Appl. No. 15/436,651, 40 pages (dated Nov. 15, 2017).
Bruce D. Sunstein, Esq. Sunstein Kann Murphy & Timbers LLP, Response B and Declaration of Manijeh Goldberg, Ph.D.—U.S. Appl. No. 15/436,651, 151 pages (filed Jan. 23, 2018).
Final Office Action—U.S. Appl. No. 15/436,651, 26 pages (dated Apr. 30, 2018).
Bruce D. Sunstein, Esq. Sunstein Kann Murphy & Timbers LLP, Response C and Request for Consideration Under the After Final Consideration Pilot Program 2.0, U.S. Appl. No. 15/436,651, 26 pages (filed May 21, 2018)
Patrea L. Pabst Pabst Patent Group LLC, Amendment and Response to Final Office Action—U.S. Appl. No. 14/186,977, 11 pages (dated Sep. 23, 2016).
Non-Final Office Action—U.S. Appl. No. 14/186,977, 11 pages (dated Jun. 22, 2016).
Mohandas et al., "Drug loaded bi-layered sponge for wound management in hyperfibrinolytic conditions," Journal of Materials Chemistry B, pp. 5795-5805, Jun. 10, 2015.
Lee et al., "Controlled-release of tetracycline and lovastatin by ploy (D, L-lactide-co-glycolide acid)—chitosan nanoparticles enhances periodontal regeneration in dogs," International Journal of Nanomedicine, pp. 285-297, Jan. 18, 2016.
CocoaBio Tech., "Preparation and Use of a Dry Ice/Ethanol Bath," 2 pages, retrieved from the Internet on Aug. 29. 2018 [https://www.koko.gov.my/CocoaBioTech/GeneralLab4.html].
LarkinWeb, "Lab freezing bath temperatures," 3 pages, retrieved from the Internet on Aug. 29, 2018 [https://larkinweb.co.uk/science/freezing_bath_tempreatures.html].
Sigma-Aldrich., "Hanks' Balanced Salts," Sigma-Aldrich, 1 page, retrieved from the Internet in Apr. 2007 [https://www.sigmaaldrich.com/content/dam/sigmaaldrich/docs/.../1/h1387pis.pdf].
Goldberg et al., "Development of a Nanoparticle-Embedded Chitosan Sponge for Topical and Local Administration of Chemotherapeutic Agents," Journal of Nanotechnology in Engineering and Medicine, 11 pages, retrieved from the Internet on Nov. 4, 2017 [https://nanoengineeringmedical.asmedigitalcollection.asme.org/].
Miyazaki et al., "Oral mucosal bioadhesive tablets of pectin and HPMC: in vitro and in vivo evaluation," International Journal of Pharmaceutics, pp. 127-132, Jun. 15, 2000.
Engineering 360, "Acrylic Adhesives and Acrylate Adhesives Information," 2 pages, retrieved from the Internet on Nov. 6, 2017 [https://www.gloabalspec.com/learnmore/materials_chemicals/adhesives/acrylic_methacrylate_adhesives, accessed].
Luangtana-Anan et al., "Effect of Chitosan Salts and Molecular Weight on a Nonoparticulate Carrier for Therapeutic Protein," Pharmaceutical Development and Technology, pp. 189-196, 2005.
Galante et al., "About the Sterilization of Chitosan Hydrogel Nanoparticles," PLOS One, pp. 1-18, Dec. 21, 2016.
Lee et al., "Equilibrium and kinetic studies of copper(II) ion uptake by chitosan-tripolyphosphate chelating resin," Polymer, pp. 1879-1892, 2001.
Kotiyan et al. "Snythesis and Characterization of an Acrylate Pressure Sensitive Adhesive for Transdermal Drug Delivery," Polymers for Advanced Technologies, pp. 137-143, 2002
Barat et al., "Chitosan inserts for periodontitis; Influence of drug loading, plasticizer and crosslinking on in vitro metronidazole release," pp. 469-477, 2007.
Kasper et al, The Freezing Step in Lyophilization: Physico-chemical Fundamentals, Freezing Methods and Consequences on Process Performance and Quality Attributes of Biopharmaceuticals, 78(2):248-263, Jun. 2011.
Patapoff et al., The Importance of Freezing on Lyophilization Cycle Development, 15(3):16-22, Mar. 15, 2002.
Weng et al, Burns: Types, Treatments, and More, 15 pages, 2016.
International Search Report and Written Opinion of PCT Application No. PCT/US2022/031790, 9 pages, dated Aug. 18, 2022.
International Search Report and Written Opinion received for PCT Application No. PCT/US2021/012015, 15 pages.
Amasya Gulin et al., "Bioadhesive and Mechanical Properties of Triamcinolone Acetonide Buccal Gels", Journal of Pharmaceutical Sciences, 2012, 9(1), 1-12.

* cited by examiner

PARTICLE-BASED MULTI-LAYER THERAPEUTIC DELIVERY DEVICE AND METHOD

CROSS REFERENCE TO RELATED APPLICATIONS

The present application is a divisional of U.S. patent application Ser. No. 15/932,315 filed Feb. 16, 2018 and claiming the benefit of U.S. provisional application No. 62/460,665, filed on Feb. 17, 2017. The disclosures of these applications are incorporated herein by reference in their entirety.

STATEMENT REGARDING FEDERALLY SPONSORED RESEARCH

This invention was made with government support under grants nos. R44CA192875-01 and number R44DE023725-03 awarded by The National Institutes of Health. The government has certain rights in the invention.

TECHNICAL FIELD

The present invention relates to multi-layer devices for delivery of one or more therapeutic agent to an epithelial tissue, and in particular to devices with a layer that features a porous polymeric matrix including chitosan and a plurality of particles embedded within the matrix.

BACKGROUND

Despite advances in technology, there exists a significant need for customized medicine and alternative agent delivery methods. Bruising, pain, scarring, burns, open sores, mucositis, and oral and skin cancers such as melanoma are all examples of conditions which are topically accessible due to their occurrence on epithelial tissue such as skin or mucosa. These conditions are usually localized to readily accessible regions of the skin or mucosa. In spite of this accessibility, agents used for the treatment or pain mitigation of these conditions are frequently administered either via oral consumption (for example aspirin for the relief of pain or agents for the relief of inflammation), or intravenously (for the treatment of cancer).

Burns are a significant problem both in the US and worldwide. Burns are one of the most common injuries that occur within households, and in particular among children. While irritation refers to a painful region on the surface of the skin, burns consist of both a highly sensitive, painful area as well as severe skin damage which causes affected cells to die. The severity of burns is categorized in degrees from 1 to 4. First degree burns consist of red, painful non-blistered skin. The skin may peel over the following days and turns white when pressure is applied. Second degree burns are thicker and usually result in blisters forming on the skin. The skin likewise may swell and will appear thick. Third degree burns include a widespread thickness with a leathery white appearance and deeper penetration. Fourth degree burns are the most severe, extending past the skin and into the surrounding tendons and/or bones. These burns are usually caused by boiling liquids, fires, and electrical/chemical accidents.

Psoriasis is another condition which affects the skin with few ideal treatment options. Psoriasis is an autoimmune disease that causes raised, red scaly patches to appear on the skin. It has been linked to the presence and combination of multiple genes that are present in 1 in 10 people. It usually affects elbows, knees, and the scalp, and causes itching, burning or stinging sensations. Flares of psoriasis are usually triggered by some stimulus, which can include stress, skin injury, infection, and certain medications including lithium, antimalarials, inderal, quinidine and indomethacin. While ointments and creams have been marketed to treat psoriasis symptoms and flares, there are no successful methods of controlled, longer term treatment of psoriasis.

Melanoma is a cancer of the melanocyte cells that comprise human skin. Melanocytes make the brown pigment called melanin which gives the human skin its brownish color. It also protects deeper layers from the sun. Melanoma is frequently hard to detect because it resembles the appearance of moles and can be difficult to spot. Melanoma is primarily caused by intense, occasional UV exposure of these cells, with genetic factors playing a role. Approximately 10,130 people die annually in the United States from melanoma. The cancer is most common on the chest and back (in men) and on the legs (in women), as well as the face and neck in both men and women.

Mucositis is another topically assessable condition that often results from chemotherapy and radiation treatments given to patients. It primarily consists of highly painful inflammation and ulceration of mucous membranes. It is caused by the rapid breakdown of the rapidly divided epithelial cells within the gastrointestinal tract, which includes the topically accessible and sensitive oral cavity. The oral mucosa is one of the most sensitive parts of the body and is particularly vulnerable to chemotherapy and radiation. As such, it is the most common location for mucositis and among the most common complication resulting from cancer treatments. Oral mucositis can lead to pain, nutritional problems due to the lack of an ability to eat, increased risk of infection, and can be dose-limiting.

Oral cancer is also a significant and growing problem which affects the topically accessible oral cavity. Within America alone, approximately 40,000 Americans will be diagnosed with oral and pharyngeal cancer this year, approximately 8,000 will die, and significantly more will be affected by associated pain and side effects of current treatment methods. Over 640,000 new cases each year are estimated worldwide. While the incidence of many cancers is decreasing, the incidence of oral cancer continues to increase, in part because of the lifestyle choices in many eastern nations (smoking, tobacco and alcohol use), as well as the increasing incidence of oral HPV within developed nations. Particular strains of oral HPV have been found to cause oral cancer, and its spread within developed western nations has further compounded this epidemic.

Current treatment methods are frequently ineffective and can cause damage to the body. In addition, when surgery is used, permanent disfiguration can occur after surgical resection of oral tumors. The patient s ability to eat, drink, or properly speak after surgery can also become impaired or not possible. Emotional debilitation associated with facial reconstruction is high, as reconstruction affects the face, neck or other regions affected by the large removal of tissue. These can include jawbone or oral tissue reconstruction. Further, these procedures can also leave the patient hospitalized in recovery for long periods of time. New, more targeted methods of treatment, including combination therapies are needed to solve these problems.

In addition to monetary cost, pain and physical side effects associated with the conditions above, emotional side effects also speak to the especially tragic and debilitating effect these conditions. The emotional toll for patients with these diseases can be great. For example, surgery during the treatment of oral cancer can be painful and permanently disfiguring. Hair loss, hearing problems, kidney damage and reproductive organ damage associated with chemotherapy used to treat melanoma and oral cancer is highly debilitating. Mucositis is a common side effect of chemotherapy and radiation therapy, and can last for long periods of time while these treatments take place. Mucositis is very painful, and can inhibit eating, drinking, and speech.

The conditions described above represent significant topically-accessible diseases with which traditional treatment methods are not ideal. While localized topical treatments exist for a number of these conditions, such as topical creams or ointments for the treatment of open sores, burns or mucositis, they also pose notable shortcomings in terms of efficacy. These include permeation, duration of treatment, and lack of effective delivery of therapeutic compositions featuring a combination of agents. Ointments and patches are able to provide an initial bolus dose of an agent followed by a rapid decline in delivery, leading to uneven doses. Multiple doses are often required as a result, which leads to poor compliance and variability. Permeation can also hinder the efficacy of ointments and patches, and local retention to the applied region can also vary.

SUMMARY OF THE EMBODIMENTS

In accordance with embodiments of the invention, there is provided a device for delivery of a first therapeutic agent and a second therapeutic agent to a site in epithelial tissue. The device includes a first layer including a first porous, mucoadhesive, freeze-dried polymeric matrix having first and second opposed surfaces. The first matrix is formed by a composition including chitosan, a hydration promoter, a particle adhesion inhibitor, and a particle aggregation inhibitor. The first layer also includes a plurality of first particles embedded within the first matrix so as to be directly surrounded by, and in contact with, the first matrix, the first particles containing the first therapeutic agent and having a coating around the first therapeutic agent, the coating including chitosan so as to provide controlled release of the first therapeutic agent from the first particles through one of the opposed surfaces of the first matrix. The device also includes a second layer, adjacent to the first layer. The second layer includes a second, freeze-dried polymeric matrix having third and fourth opposed surfaces, the second matrix containing the second therapeutic agent. The first layer or the second layer, or each the first layer and the second layer are configured to be attached to the site in the epithelial tissue. The second matrix may be formed by a composition including chitosan, and may also include a plurality of second particles embedded within the second matrix, where the second particles contain the second therapeutic agent. The second particles may have a coating around the second therapeutic agent, the coating including chitosan. In embodiments of the device, the hydration promoter may be one or more of ethylene glycol, propylene glycol, and beta-propylene glycol. In embodiments of the device, the particle adhesion inhibitor may be a non-ionic polymer, such as hydroxypropylmethylcellulose (HPMC). In embodiments of the device, the particle aggregation inhibitor may be one or more of a monosaccharide, disaccharide, sugar alcohol, chlorinated monosaccharide, and chlorinated disaccharide. In embodiments of the device, the first particles may further include sodium tripolyphosphate. One or both of the opposed surfaces of the first matrix may be permeable to water. Alternatively, or in addition, one or both of the opposed surfaces of the second matrix may be permeable to water. In embodiments of the device, the average diameter of the first particles may be from about 55 nm to about 395 nm. In embodiments of the device, the first therapeutic agent and the second therapeutic agent may be the same therapeutic agent. In embodiments of the device, at least one of the first therapeutic agent and second therapeutic agent is a chemotherapeutic agent. In embodiments of the device, the chitosan of the first particles may be pure chitosan. In embodiments of the device, the first matrix may also include a free amount of the first therapeutic agent. In embodiments of the device, the particle aggregation inhibitor may be in a concentration of 0.1% to 50% by weight of the first matrix. In accordance with embodiments of the device, the hydration promoter, the particle adhesion inhibitor, and the particle aggregation inhibitor are compounds mutually distinct from one another and present in amounts sufficient to achieve the controlled release of the first particles without preventing formation of the freeze-dried first matrix. In representative embodiments, the first surface of the first matrix may be configured to be attached to the site in the epithelial tissue and the first matrix may be configured to provide controlled release of the first particles, through the first surface, when the first surface of the first matrix is thus attached to the site. In embodiments of the device, the fourth surface of the second matrix may be configured to be attached to the site in the epithelial tissue and the second matrix may be configured to provide controlled release of the second particles, through the fourth surface, when the fourth surface of the second matrix is thus attached to the site.

In accordance with embodiments of the invention, there is provided a method for manufacturing a multi-layer device for delivery of a first therapeutic agent and a second therapeutic agent to a site in epithelial tissue. The method includes: forming a first precursor mixture including a first polymeric matrix precursor and the first therapeutic agent, where the first polymeric matrix precursor includes a plurality of particles, chitosan, a hydration promoter, a particle adhesion inhibitor, and a particle aggregation inhibitor, the plurality of particles containing the first therapeutic agent and have a coating around the first therapeutic agent, the coating including chitosan; forming a second precursor mixture including a second polymeric matrix precursor and the second therapeutic agent; freezing the first precursor mixture and the second precursor mixture in a bath containing an aqueous alcoholic solution at a temperature above the freezing temperature of the aqueous alcoholic solution and at most −40° C., to form a combined solid including a frozen first layer precursor adjacent to a frozen second layer precursor; and drying the combined solid to form the multi-layer device, where the multi-layer device includes a first layer including a first polymeric matrix with the plurality of particles embedded within the first polymeric matrix and a second layer including a second polymeric matrix. The first layer, the second layer, or both, are configured to be attached to the site in the epithelial tissue. The freezing of the first precursor mixture may take place prior to the freezing of the second precursor mixture. In embodiments of the method, the bath may also contain dry ice. In embodiments of the method, the aqueous alcoholic solution may include about 90 wt % ethanol to about 99 wt % ethanol. In embodiments of the method, the second polymeric matrix precursor may be chitosan. In embodiments of the method, the drying may be under vacuum.

In accordance with embodiments of the invention, there is provided a method for manufacturing a multi-layer device for delivery of a first therapeutic agent and a second therapeutic agent to a site in epithelial tissue. The method includes: forming a first precursor mixture including a first polymeric matrix precursor and the first therapeutic agent, where the first polymeric matrix precursor includes a plurality of particles, chitosan, a hydration promoter, a particle adhesion inhibitor, and a particle aggregation inhibitor, the plurality of particles containing the first therapeutic agent and having a coating around the first therapeutic agent, the coating including chitosan; forming a second precursor mixture including a second polymeric matrix precursor and the second therapeutic agent; freezing the first precursor mixture in a first mold containing a first aqueous alcoholic solution at a temperature above the freezing temperature of the first aqueous alcoholic solution and at most −40° C., to form a frozen first layer precursor; freezing the second precursor mixture in a second mold containing a second aqueous alcoholic solution at a temperature above the freezing temperature of the second aqueous alcoholic solution and at most −40° C., to form a frozen second layer precursor; applying a salt solution to a portion of the frozen first layer precursor, the frozen second layer precursor, or both, to form a coating on the portion; combining the frozen second layer precursor with the frozen first layer precursor, to form a combined solid; and drying the combined solid to form the multi-layer delivery device, where the multi-layer device includes a first layer that includes a first polymeric matrix with the plurality of particles embedded within the first polymeric matrix and a second layer that includes a second polymeric matrix, where the first layer or the second layer is configured to be attached to the site in the epithelial tissue. The method may further include combining a third layer precursor with the combined solid, to form a combined solid including the first layer, the second layer, and a third layer. In embodiments of the method, the salt solution may be saline. In embodiments of the method, the second polymeric matrix precursor may be chitosan. The first aqueous alcoholic solution and the second aqueous alcoholic solution may be the same solution.

BRIEF DESCRIPTION OF THE DRAWINGS

The foregoing features of embodiments will be more readily understood by reference to the following detailed description, taken with reference to the accompanying drawings, in which:

FIG. 5A is an image that shows fluorescent FITC and Cy5 above the tissue shortly after application of the device. FIG. 5B is an image that shows FITC beginning to permeate the tissue after 30 minutes. FIG. 5C is an image that shows the green FITC permeating deeper into the tissue after 1 hour.

DETAILED DESCRIPTION OF SPECIFIC EMBODIMENTS

Definitions

Figure 1:
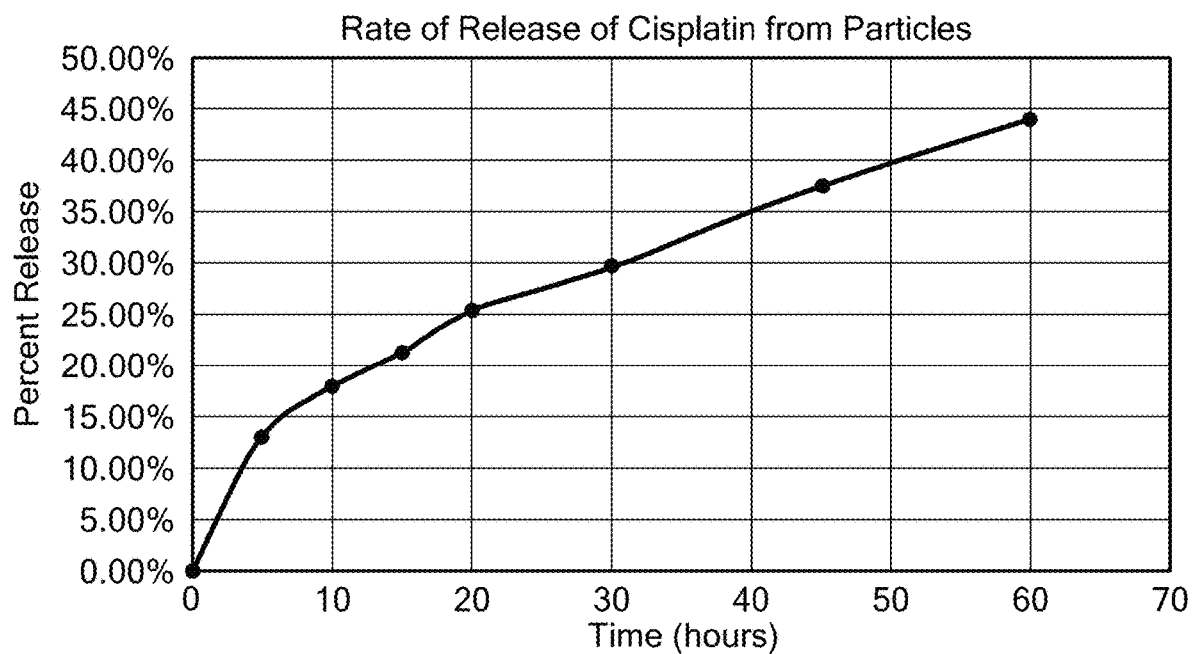
FIG. 1 is a graph showing the release profile of one embodiment of particles having an average diameter in the range of 500 to 2000 nm which may be included within a multi-layered device according to embodiments of the present invention. The graph shows the rate of release of the encapsulated agent from the particles over 60 hours. Cisplatin was used for this experiment due to its use in the treatment of oral cancer and its ease of detection via atomic absorption spectrometry (AAS). Cisplatin is platinum-based, and AAS can detect amounts of platinum as small as 5 µg/L. The graph shows 45% of cisplatin released from Particles over 60 hours.

As used in this description and the accompanying claims, the following terms shall have the meanings indicated, unless the context otherwise requires:

A "polymer" is a molecule having at least 100 units of a monomer.

"Particles" herein typically have an average diameter of at least 1 nm to at most 2000 nm. Particles having an average diameter below 200 nm may also be referred to as "nanoparticles," while particles having an average diameter of at least 200 nm to at most 2000 nm may also be referred to as "microparticles."

A "particle diameter" or "particle size" is the length of the longest straight axis between two points on the surface of the particle.

A "pure chitosan" is a chitosan that is not a salt of chitosan.

A "particle adhesion inhibitor" is an additive that lowers the attractive forces between a polymeric matrix and particles embedded therein. As a result, the particles can move through the matrix at a faster rate than in the absence of the adhesion inhibitor.

A "particle aggregation inhibitor" is an additive that lowers the tendency of particles embedded in a matrix to aggregate when the matrix is subjected to freezing. As a result, the particles are less likely to suffer from damage or destruction when the freezing takes place.

A "mucoadhesive" material is characterized as having the ability to adhere to mucosal membranes in the human body.

A matrix is "porous" when a fraction of its volume is void space. In some instances, the void space is accessible from the outer surface of the matrix, so that items present in the void space, such as particles, may migrate to and from the outer surface.

"Mucosal tissue" is tissue having an associated mucosa. In particular, mucosal tissue includes the mucosa and also tissue underlying the mucosa. A "site in mucosal tissue", where, for example, a cancerous tumor is present may involve not only the mucosa but also tissue underlying the mucosa.

"Polydispersity index" (PDI) or simply, "dispersity" is a measure of the heterogeneity of sizes of a set of particles, for example particles in a mixture.

"Zeta potential" (ZP) is a measure of the overall charge that a particle acquires in a particular medium. The ZP may be measured on a Zetasizer Nano instrument.

"Permeation" is the ability to pass through or penetrate a mucosa, its underlying tissue, or both.

"Biocompatible" refers to the ability of a biomaterial to perform its desired function with respect to a medical therapy, without eliciting any significant undesirable local or device effects in the recipient or beneficiary of that therapy, but generating the most appropriate beneficial cellular or tissue response in that specific situation, and optimizing the clinically relevant performance of that therapy.

"HPMC" refers to hydroxypropyl methylcellulose, also known as hypromellose.

"Biodegradable" refers to a property of the materials that is capable of being broken down especially into innocuous products by the action of living things.

"Kilo count per second" (Kcps)", mean count rate (in kilo counts per second (kcps)). For example, the threshold may be set such that when the count rate of the sample is lower than 100, the measurement should be aborted, meaning the concentration of the sample is too low for measurements. A sample with suitable Kcps can be considered a stable sample with idea concentration for measurement.

"Mesh" refers to a device, sponge, wafer, or like product which contains elements incorporated within it to be released from the mesh when it is applied to a mucosa.

"Multi-layered" is used herein to refer to items having more than one layer.

"Device" refers to a thing which is made for a particular purpose.

A "device for delivery of a therapeutic agent based on a polymeric matrix and particles" may also be referred to as an "agent delivery device" or as a "delivery patch".

"Sustained delivery" refers to a consistent rate of delivery of an agent to a site.

"Saline" is used herein to refer to an aqueous solution of sodium chloride. For example, "0.12% saline" refers to a saline having 1.2 grams of sodium chloride per liter solution.

Unless otherwise specified, the term "wt %" refers to the amount of a component of a device for delivery of a therapeutic agent, as expressed in percentage by weight.

Unless otherwise specified, the "molar mass" of a polymer is intended to mean the number average molar mass of the polymer molecules.

Unless otherwise specified, the term "nm" refers to nanometer(s).

Multi-Layer Matrix and Particle Device

In a first aspect, the present application provides a multi-layered device which is able to separately deliver two or more agents and provide a consistent, sustained agent delivery, thus mitigating issues associated with traditional topical delivery devices. The device is capable of delivering the same or multiple agents in phases over a period of time or delivering multiple agents concurrently via modulation of the makeup of each layer. The device and methods for its manufacturing have been developed to address the unmet need of delivering agents in a multitude of forms locally to mucosal and skin tissue. The multiple layers within this platform may be used for delivering any therapeutic, prophylactic, diagnostic or nutraceutical agent which is capable of encapsulation and release on epithelial tissue. Representative agents include biologics, peptides, nucleotides, anti-infectives, antibiotics, antifungals, antivirals, anti-inflammatories, immunomodulators, vaccines, and combinations thereof.

Figure 8:
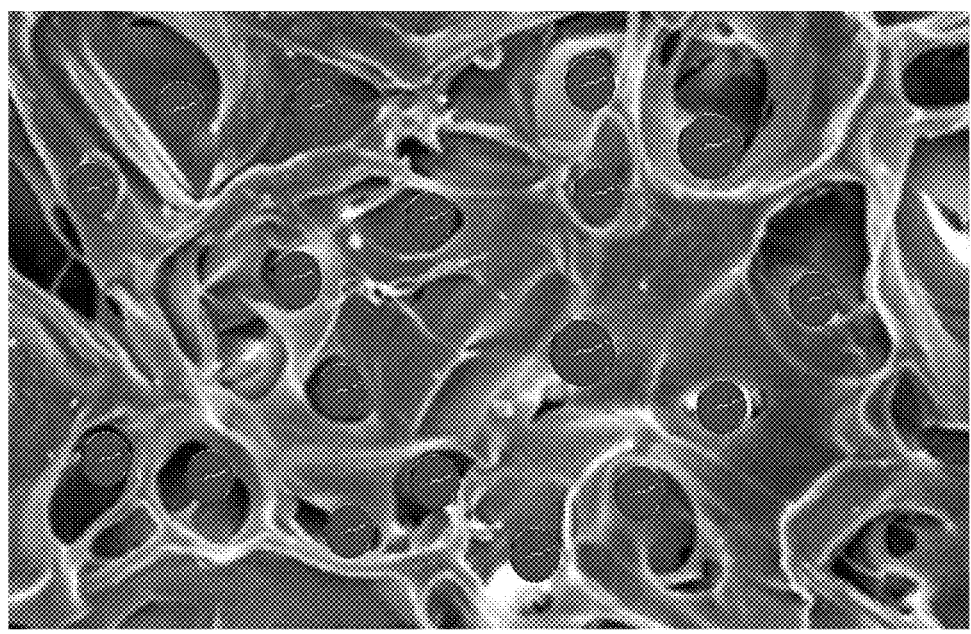
FIG. 8 shows a polymeric matrix containing particles inside of it according to embodiments of the present invention.
Figure 9:
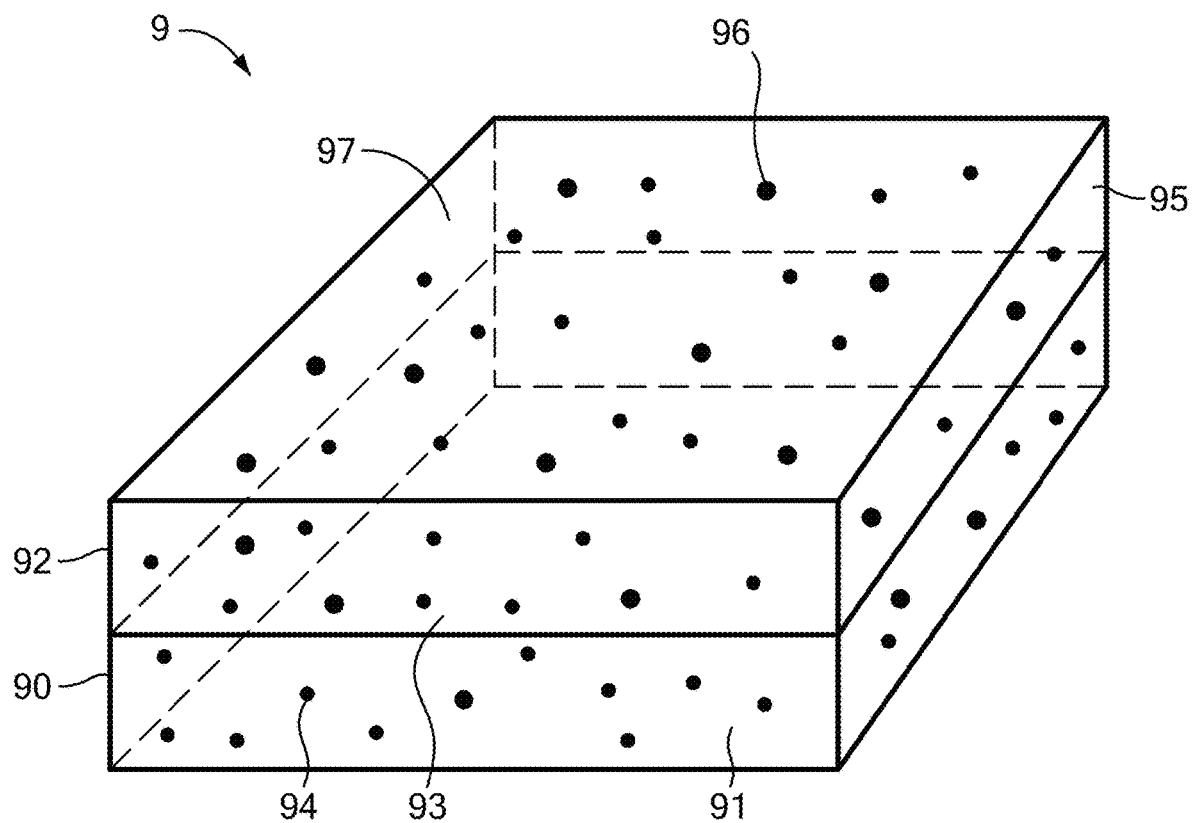
FIG. 9 is a schematic illustration of an exemplary two-layer device.

As illustrated in FIG. 9, an example device 9 includes at least a first layer 90 containing a first therapeutic agent and a second layer 92 containing a second therapeutic agent. At least one of the layers of the device, for example the first layer 90, includes a first porous, mucoadhesive polymeric matrix that is formed by freeze-drying a composition including chitosan. Particles 94 are embedded within the first matrix. As further illustrated in FIG. 8, the particles are directly surrounded by, and in contact with, the first matrix. The particles 94 contain the first therapeutic agent and have a coating around the first therapeutic agent, the coating including chitosan so as to provide controlled release of the agent from the particles.

Representative examples of the matrix and particles of the first layer are U.S. patent application Ser. No. 15/436,651, published as U.S. Patent Appl. Publ. No. 2017/0239189, where chitosan particles embedded in a chitosan-based matrix are disclosed. This prior application is hereby incorporated herein by reference in its entirety; however, the definitions provided above in paragraph 21 shall prevail over any contrary definitions in the prior application. Chitosan is a deacetylated derivative of chitin, the second most abundant polysaccharide, and has a large density of reactive groups and a wide range of molecular weights. Chitosan is considered useful as a bioadhesive material because of its ability to form non-covalent bonds with biological tissues, mainly epithelia and mucous membranes. Bioadhesions formed using natural polymers have unique properties as a carrier because they can prolong residence time and, therefore, increase the absorbance of loaded drugs. Chitosan is a bioabsorbable, biocompatible, biodegradable, anti-bacterial and non-toxic polymer.

In addition, chitosan has different functional groups that can be modified. Because of its unique physicochemical properties, chitosan has great potential in a range of biomedical applications. Chitosan can be used as a delivery mechanism because of its bio-adhesiveness as well as its established ability to act as an absorption and permeation enhancer. The barrier in mucosa or epithelium can easily be disrupted by chitosan particles, enhancing permeability through mucosa.

The most widely developed particle manufacturing methods are ionotropic gelation and self-assembling polyelectrolytes. These methods offer many advantages such as simple and mild preparation method without the use of organic solvent or high shear force. They are applicable to broad categories of agents including macromolecules which are notorious as labile agents. Usually, the factors found to affect particles formation, including particle size and surface charge, are molecular weight and degree of deacetylation of chitosan. The particles may be tailored to be stable in a variety of environments.

The ionotropic gelation method is commonly used to prepare chitosan particles. This method is based on electrostatic interaction; at physiologic pH, the primary amine groups of chitosan are protonated, and therefore chitosan is positive-charged. The positive charge is used to form particles in solution via cross-linking with polyanions (stabilizer) such as sodium tripolyphosphate (STPP), to efficiently encapsulate the drug via electrostatic interaction, and to promote cellular internalization of drug-containing chitosan particles. Several advantages of this simple and mild method include the use of aqueous solutions, the preparation of particles with a small size, the manipulation of particle size by the variation in pH values, and the possibility of encapsulation of drug during particle formation. Structural changes can be introduced by ionic strength variations like presence of KCl at low and moderate concentrations emphasize swelling and weakness of chitosan-STPP ionic interactions, in turn particle disintegration.

The particles 94 (micro- but also nano-sized particles) can permeate epithelial tissue such as mucosa or skin. The particle size is dependent on the pH of the solution and the weight ratio of Chitosan to STPP, and the size of the particles influences the drug release rates. Other parameters affect the particles including the chitosan: stabilizer (such as STPP) ratio in aqueous solution during the synthesis process, as an increase in the amount of stabilizer leads to a higher degree of chitosan cross-linking and a decrease in the particle dimensions.

The first layer 90 is improved over traditional particle-based devices by the addition of a hydration promoter to the first matrix. Example hydration promoters include hygroscopic compounds such as glycols, for instance ethylene glycol, propylene glycol, beta-propylene glycol, and glycerol. Exemplary concentration ranges for the amount of hydration promoter include from about 0.001 to about 10 wt %, from about 0.01 to about 5 wt %, and from about 0.1 to about 1 wt %.

Without wishing to be bound to any particular theory, it is believed that the hydration promoter increases moisture absorption by the device first layer 90. This increase in hydration enables the rapid release and permeation of the particles 94 from the first polymeric matrix. It is also believed that the hydration promoter improves uniformity and durability by acting as a cryoprotectant during the manufacturing process of the delivery device. Again without being bound to any particular theory, it is believed that the hydration promoter acts as a "spacer" between ice crystals and matrix polymer molecules, to ensure a uniform freezing pattern. The resulting structure is more flexible, uniform, and durable than in the absence of the hydration promoter.

The first layer 90 may be also improved by the addition of an adhesion inhibitor. Without wishing to be bound to any particular theory, it is believed that when the first matrix and particles are made of materials bearing polar or ionically charged moieties, such as chitosan, the mobility of the particles suffers. In the instance of chitosan, it is believed that the interactions between acetyl and amine moieties of the polymer cause the particles to adhere to the matrix and inhibit their release.

It has been found that the inclusion of an adhesion inhibitor can mitigate adhesion of the first matrix with the particles. Without being bound to any particular theory, it is believed that the adhesion inhibitor acts as a "spacer" between the chitosan of the particles and the chitosan in the body of the matrix, releasing the particles and allowing for improved drug release profiles. Representative example adhesion inhibitors include non-ionic polymers such as hydroxypropyl methylcellulose (HPMC). Depending on the application, the molar mass of the non-ionic polymer may be from about 1 kDa to about 200,000 kDa, while its viscosity may vary from about 10 cps to 100,000 cps. In representative embodiments, the molar mass of the non-ionic polymer is from about 10 kDa to 30 kDa, and its viscosity from about 10 cps to about 100 cps. Depending on the application, the amount of adhesion inhibitor may be from about 0.1 wt % to about 99 wt %. In some embodiments, the amount of adhesion inhibitor is from about 0.1 wt % to about 25 wt %.

A further improvement of the delivery devices may be attained by the addition of an aggregation inhibitor. Processes for manufacturing the delivery devices include freezing steps during which ice crystals may form within the first matrix. Such crystals can force the particles into each other, creating particle aggregates where the particles are damaged or destroyed. Again without wishing to be bound to any particular theory, it is believed that aggregation inhibitors exert a cryoprotectant action by forming crystal microstructures which prevent aggregation of the particles. Carbohydrates and carbohydrate derivatives provide exemplary types of aggregation inhibitors, including monosaccharides, disaccharides, sugar alcohols, chlorinated monosaccharides, and chlorinated disaccharides such as sucralose. Depending on the application, the amount of aggregation inhibitor in the patch may be in the range from about 0.1 to about 50 wt %. In some embodiments, the amount of aggregation inhibitor is from about 1 to about 10 wt %.

In another set of representative embodiments, the particles are improved pure chitosan particles. Traditional chitosan particles are manufactured with salts of chitosan characterized by a high degree of deacetylation and bearing electrically charged moieties, for example chitosan chloride and chitosan glutamate. It has been found that better results are provided if the particles are made from pure chitosan, a material characterized by not being a salt, that is, with its amine groups unprotonated, and having a degree of deacetylation of at least 70%. In particular, the particles are characterized by larger diameters than traditional particles. In some embodiments, the average diameter of the pure chitosan particles may range from about 200 to about 2000 nanometers. In other embodiments, the average diameter ranges from about 500 to about 2000 nanometers, and in additional embodiments from 500 to 1000 nm.

In a further improvement, the chitosan particles are improved by the addition of sodium tripolyphosphate (STPP). Without wishing to be bound to any particular theory, it is believed that the STPP functions as a cross-linker to form the particles by acting as a negative counter-ion to the positively charged amine groups on chitosan. This electrostatic interaction forms ionic bonds that support the structure of the particles. Also without wishing to be bound to any particular theory, it is believed that the presence of sodium as positive counterion renders STPP a more effective crosslinker than other TPP salts.

It has also been found that when the first matrix includes a free amount of the first therapeutic agent, embedded directly in the matrix and not otherwise coated with chitosan in the particles, the device is therapeutically more effective than comparable matrices which include either only a free amount of the first therapeutic agent or only first therapeutic agent coated with chitosan. In representative embodiments, the free amount of the first therapeutic agent constitutes between 20-80% of the total amount of therapeutic agent in the delivery device.

FIG. 1 is a graph showing the release profile of example particles having an average diameter in the range of 500 to 2000 nm. The graph shows the rate of release of the encapsulated agent from the particles over 60 hours. Cisplatin was used for this experiment due to its use in the treatment of oral cancer and its ease of detection via atomic absorption spectrometry (AAS). Cisplatin is platinum-based, and AAS can detect amounts of platinum as small as 5 µg/L. The graph shows 45% of cisplatin released from NPs over 60 hours.

The second layer 92 contains a second, freeze-dried polymeric matrix. In representative embodiments, the second polymeric matrix may be formed from a mixture including chitosan, in which case one or more of a hydration promoter, a particle adhesion inhibitor, and a particle aggregation inhibitor may also be present in the second layer. However, other polymeric matrix precursors amenable to freeze-drying are also contemplated. The second layer 94 also contains the second therapeutic agent which may be the same as or different from the first therapeutic agent.

In certain embodiments, the second layer 94 may feature second particles 96 embedded in its matrix. The particles of the second layer contain the second therapeutic agent and have a coating around the second therapeutic agent, the coating including chitosan so as to provide controlled release of the second therapeutic agent. Alternatively, a free amount of the second therapeutic agent may be embedded directly in the second matrix, and not otherwise coated with chitosan. In representative examples, the free amount of the second therapeutic agent constitutes between 20-80% of a total amount of second therapeutic agent in the device.

The first matrix of the first layer 90 has a first surface 91 and a second surface 93 opposed to the first surface 91. The second matrix of the second layer has a third surface 95 and a fourth surface 97 opposed to the third surface. In some embodiments, the second surface 93 of the first layer 90 is attached to the third surface 95 of the second layer 92. In this configuration, at least one of the first surface 91 of the first layer 90 and the fourth surface 97 of the second layer 92 may be configured to be attached to a site in the epithelial tissue of a patient, for example a site in a mucosal tissue or on the skin.

For example, when the surface that is configured to be attached to the epithelial tissue is the first surface 91 of the first layer 90, one or more of the therapeutic agents will begin to be released from the side of the first surface when it is brought into contact with the tissue. The other surface, in this instance the fourth surface 97 of the second layer 92, may be covered with a backing film, layer, or other impermeable membrane to prevent loss of therapeutic agents from the side of the device not facing the tissue, or contamination of the device via fluids or other matter. Optionally, the impermeable film, layer, or membrane may be replaced with a water-permeable film, layer, or membrane. As a further option, the fourth surface 97 includes a material selected from the group consisting of a polyacrylate adhesive, a non-woven polyester fabric, or combinations thereof.

Traditional drug delivery to epithelial tissue, such as skin or mucosa, consists of an initial bolus dose of agent followed by a steady reduction in exposure over time. The device of the present application is able to mitigate this tendency via its multiple layers and the inclusion of particles within at least one layer. The material forming the structure of each layer can be optionally chosen to degrade slowly, and the same agent (such as aspirin for the local pain mitigation of a bruise) can be chosen for inclusion within each of the multiple layers.

In this example, the device therefore can be designed to release aspirin locally to a bruise in multiple phases, providing significantly longer mitigation of pain without the side effects, multiple doses required or dose limiting hindrances associated with aspirin that is orally administered. The inclusion of particles within this device can further assist in the device's ability to provide a sustained local dosage. The particles included within this first layer are released once it is applied, permeate the skin or mucosal tissue, and remain local within the tissue beneath which the device was applied. These particles then degrade over a period of time, further providing a sustained, longer dosage of agents.

When applied within the oral cavity, the device is placed directly onto affected oral tissue within the mouth and releases agents for controlled and targeted treatment of oral diseases. Agents which may be included in free form (such as a pain mitigator in the first layer) may be designed to have an immediate effect to the underlying tissue, whereas agents encapsulated within particles (such as a therapeutic) may be included within a second or subsequent layer. The particles are then able to act independent of the first agent, permeate the underlying tissue, and provide a sustained, longer term delivery of agent to the tissue. This device overcomes deficiencies of traditional devices by offering the ability to modulate the duration and treatment order parameters to provide multiple stages and durations of treatment.

When applied to the skin, the device can be used to deliver agents for the longer-term treatment of conditions such as psoriasis and burns. Because the particles included within the device are able to release a therapeutic agent from within them over long periods of time (over 60 hours if desired), this device can be very effective in the treatment of these conditions. As shown in the example of FIG. 1, the delivery of agents from the particles during this time period is consistent and sustained.

Figure 6:
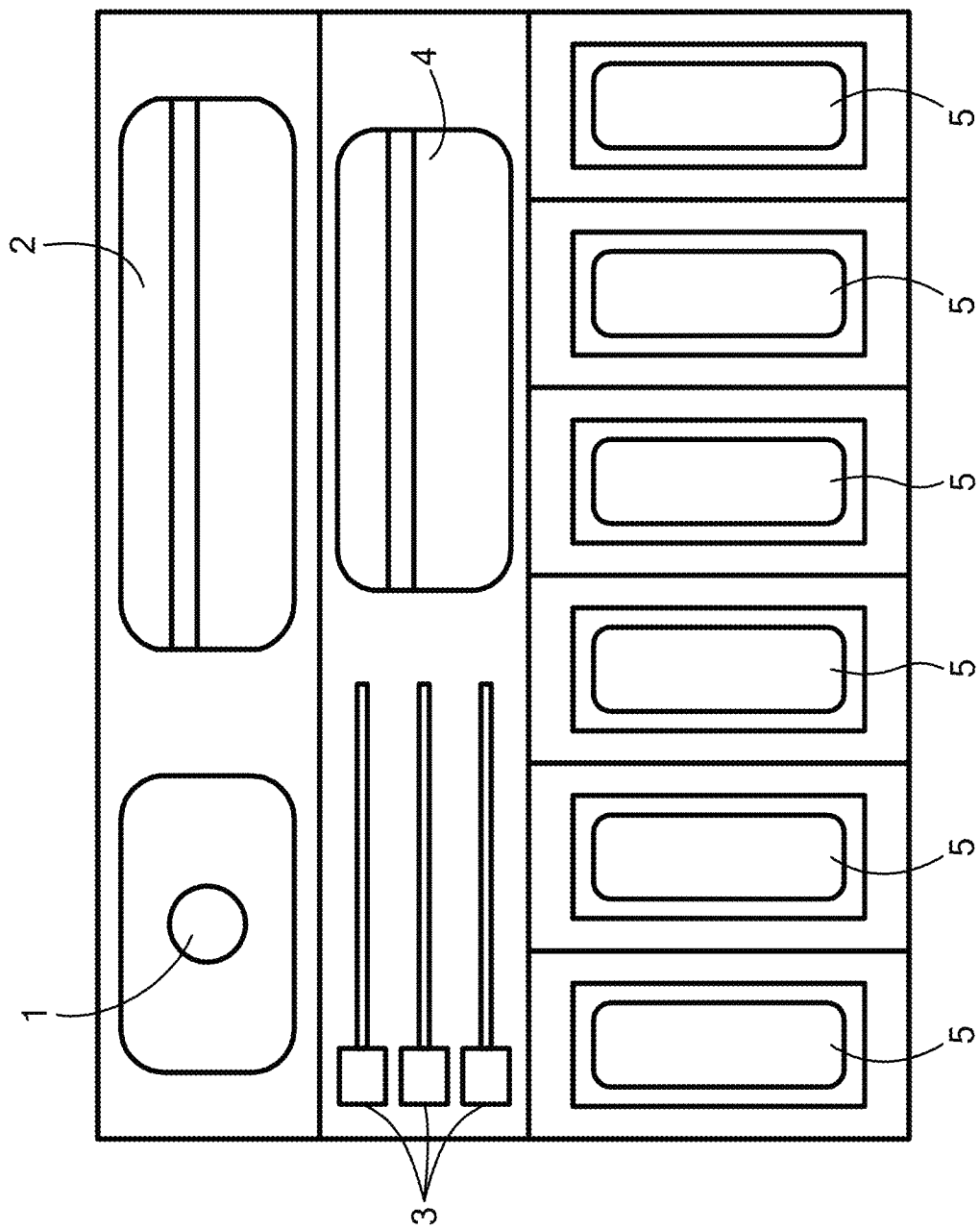
FIG. 6 shows one embodiment of the present device included as part of a larger treatment kit for use in SKIN-based indications. The depiction represents a kit containing 6 treatment devices, where: (1) refers to a wetting agent or permeation enhancer which may be externally applied to the skin prior to treatment, (2) refers to an adhesive bandage covering which may be wrapped or applied onto the device once it has been placed onto skin, acting as a bandage to ensure that the device remains in place, (3) cotton/sponge tipped applicator or dropper device used to apply the optional wetting agent/permeation enhancer, (4) A bag for disposal of hazardous waste (for use when hazardous agents are included or otherwise), and (5) refers to six individually packaged and stored treatment devices.
Figure 7:
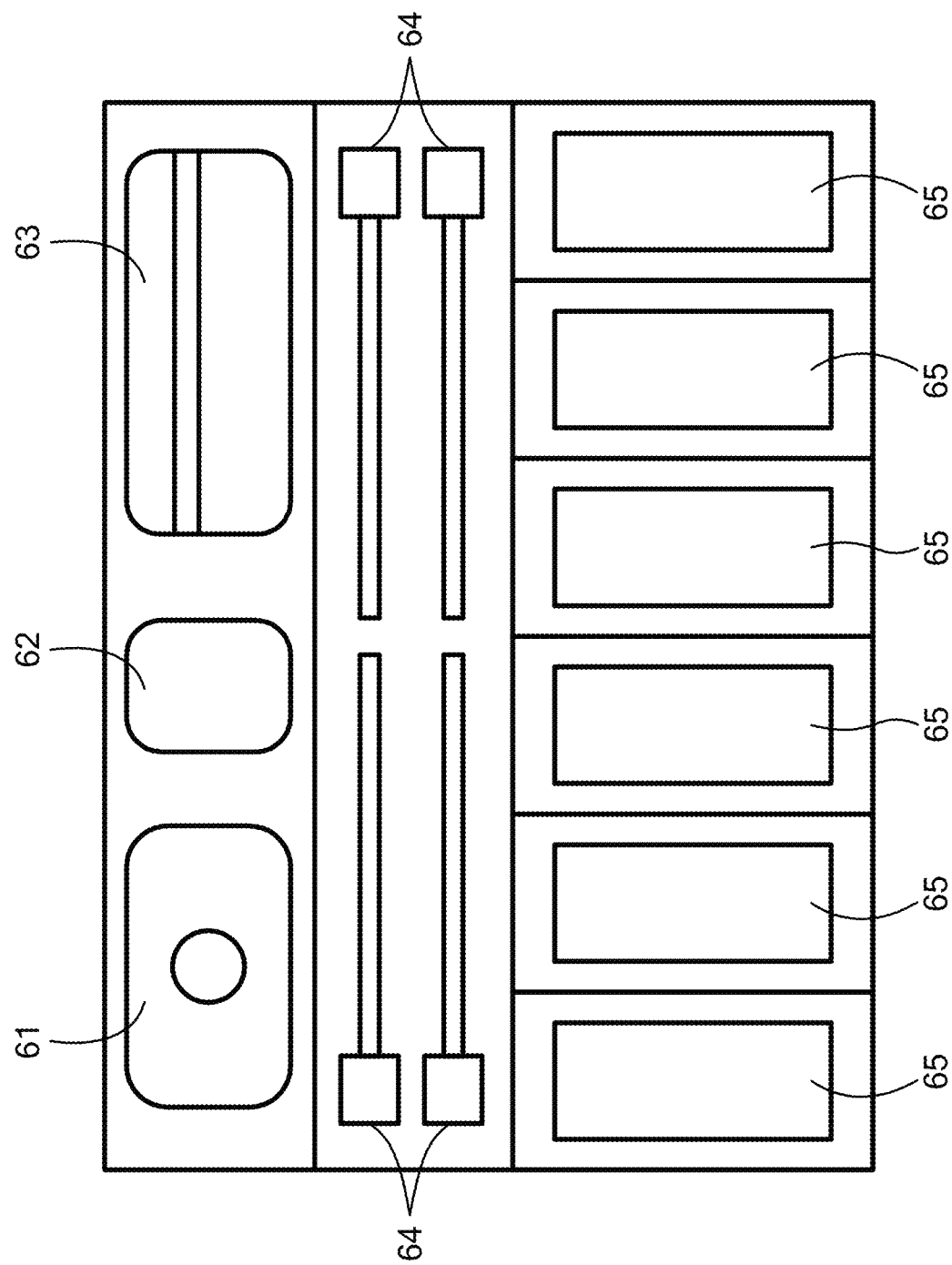
FIG. 7 represents an example multi-layer device included as part of a treatment kit for use in mucosa-based indications. The figure illustrates a kit containing six treatment devices, where: 61 refers to a wetting agent or permeation enhancer which may be externally applied to the mucosa prior to treatment (in either solution or powder form), 62 refers to gauze or other similar absorbent pad which may be used to moisten and keep the device in place within the oral cavity, 63 a bag for disposal of hazardous waste (for use when hazardous agents are included or otherwise), 64 identifies forceps or forceps-like devices used to keep the device in place and to prevent swallowing, and 65 refers to six individually packaged and stored treatment devices.

In addition, the device may be further included within a treatment kit to optimize its safety and efficacy. The kit can be optimized for a mucosa. FIG. 6 represents an example multi-layer device included as part of a treatment kit for use in mucosa-based indications. The figure illustrates a kit containing six treatment devices, where: 61 refers to a wetting agent or permeation enhancer which may be externally applied to the mucosa prior to treatment (in either solution or powder form), 62 refers to gauze or other similar absorbent pad which may be used to moisten and keep the device in place within the oral cavity, 63 a bag for disposal of hazardous waste (for use when hazardous agents are included or otherwise), 64 identifies forceps or forceps-like devices used to keep the device in place and to prevent swallowing, and 65 refers to six individually packaged and stored treatment devices.

The release of agent(s) from the device may be activated in part by exposure to moisture. Therefore, a moisturizing solution such as saline may be provided with the device to be used during the application process. Further, permeation enhancers in powder or solution form may be included to be externally applied to the mucosa prior to application of the device. The permeation enhancer may optionally be included in the form of a powder which requires reconstitution. The powdered form may be included to maintain stability of the permeation enhancer. When included in this form, the kit may optionally include additional materials among which at least one glass vial (5 mL to 20 mL in size) containing sterile water to be used for reconstitution. The kit may additionally include syringes (such as 3 mL Luer-lock syringes) and aspirating needles (such as 18G needles) to be used for reconstitution of the permeation enhancer.

In addition, when the device is used for certain indications (such as oral indications), care must be taken to ensure that the product is safely applied and removed to prevent choking or swallowing. The kit disclosed herein addresses these concerns by including all materials necessary to ensure the safe application device. Example kits include at least one pair of forceps (either multi-use metal forceps or single use disposable plastic forceps) or other similar instrument used to position and place the device to prevent exposure of agents to people or exposure of the device to the throat.

Disposable packaging can also be included within the kit to ensure the safe disposal and non-contamination of the treatment process by isolating the materials used during treatment. This packaging may include a hazardous waste package used when toxic drugs such as those used to treat oral cancer or melanoma are administered, or biohazard packaging. Additionally, empty scintillation vials may be included to collect the used device post-treatment for purposes such as residual-agent analysis.

Manufacturing a Multi-Layer Device

In representative embodiments, a method of manufacturing of a multi-layered device and a formulation created according to such method are provided. The method includes the freezing and freeze drying of polymeric solutions containing a therapeutic agent.

Precursor mixtures are first created, and then subjected to freezing or freeze drying. The device features two or more layers, as illustrated for instance in FIG. 2 and FIG. 3, and the precursor mixture to each layer may be separately made. All layers may each contain an independently chosen agent to be delivered, and at least one layer contains particles which further encapsulate at least one of the agents. The particles may be synthesized, for instance, according to the ionotropic gelation method described above, where no modification of the agent takes place. Particles are designed to range from 200 to 2000 nanometers, more preferably 500 to 2000 nanometers, and yet more preferably from 55 to 395 nanometers in average diameter so that they are able to permeate the desired surface. Agents such as a permeation enhancer, taste masking elements and agents for the formation of body structure may be added. These agents may include propylene glycol, hydroxypropylmethylcellulose, chitosan, sweeteners, peppermint or other flavorings, among many others. Solutions containing agents but no particles may also contain these and other agents.

Once ready, the precursor mixtures are subjected to freezing. It is preferable that the layers of the device be first frozen in a freezing bath of an aqueous alcohol at a temperature of at most −40° C., for example in a bath of aqueous ethanol and dry ice. This method has been found to result in a device which is able to release nearly all of its agent content and permeate deeply into the desired skin or mucosal depths. Without wishing to be bound to any particular theory, the product device is more effective as compared to other methods of freezing. When the precursor mixture was frozen via liquid nitrogen, placement in a freezer at −80° C., or standalone dry ice, some of the particles burst and the polymer in the matrix of the device became more rigid, resulting in a low percentage of agent release and a compromised therapeutic efficacy. For best results, the bath should include dry ice completely covered by a solution of at least 90 wt % ethanol in water. The precursor mixture of the first layer of the device (in liquid form) is poured into a mold, for example a silicone molding and is submerged approximately ⅔ to ¾ in the bath of ethanol and dry ice, to form a frozen layer. Preferably, about 30 minutes should be allowed to achieve complete freezing.

After freezing the initial layer, a second layer may be added by one of two methods. In the first method, the precursor mixture of the second layer is poured in liquid form on top of the frozen first layer while the first layer remains in the ethanol/dry ice bath. The resulting frozen bottom layer and liquid top layer are then submerged more deeply until a ⅔ to ¾ overall submersion ratio is met. Another about 30 minutes are allowed for complete freezing of the second layer, resulting in a combined solid featuring both frozen layers. Subsequent layers in excess of two may be added by the same process.

In the second method, each layer is separately and concurrently frozen in its individual mold within the freezing bath. After about 30 minutes are allowed to ensure complete freezing of each layer, a coating of an solution of one or more salts, for example 0.12% saline, is brushed onto the first, initial layer, to form a coating. Within about a minute of the application of the coating, the second layer is applied onto the first and a pressure of about 0.25 kg is applied. This results in a combined solid. Subsequent layers in excess of the second layer can be applied by the same method.

Figure 2:
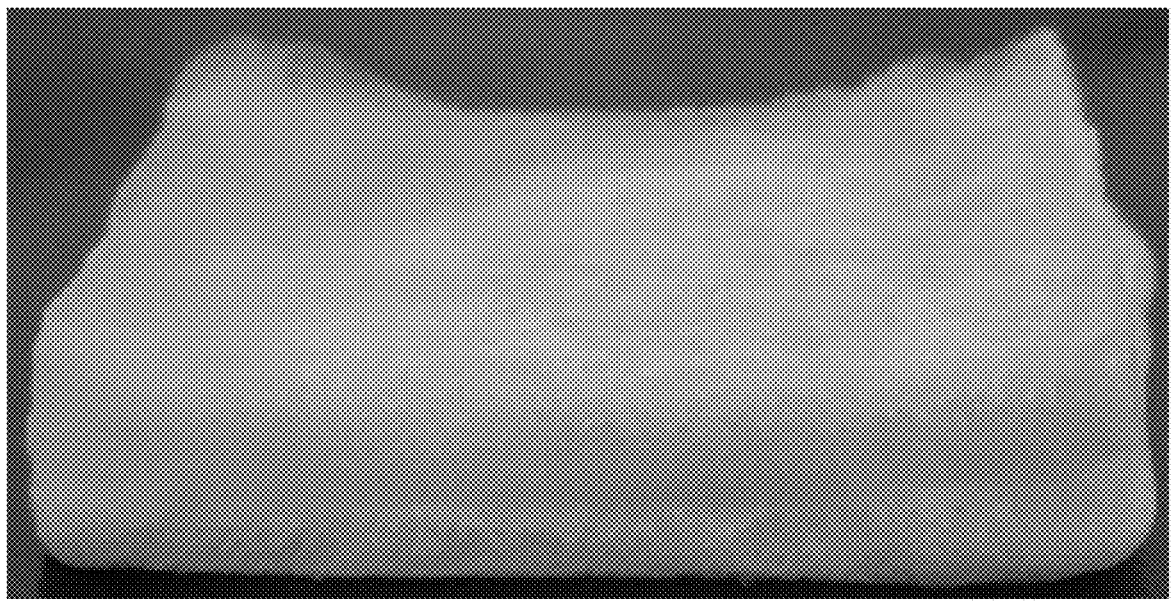
FIG. 2 is an image of an example multi-layered device according to example embodiments of the present invention. The device features two layers: one top layer including fluorescein isothiocyanate (FITC), a fluorescent dye which fluoresces green when examined under a fluorescent microscope, and one bottom layer including cyanine 5 (Cy5), a fluorescent dye which fluoresces red when examined under a fluorescent microscope.
Figure 3:
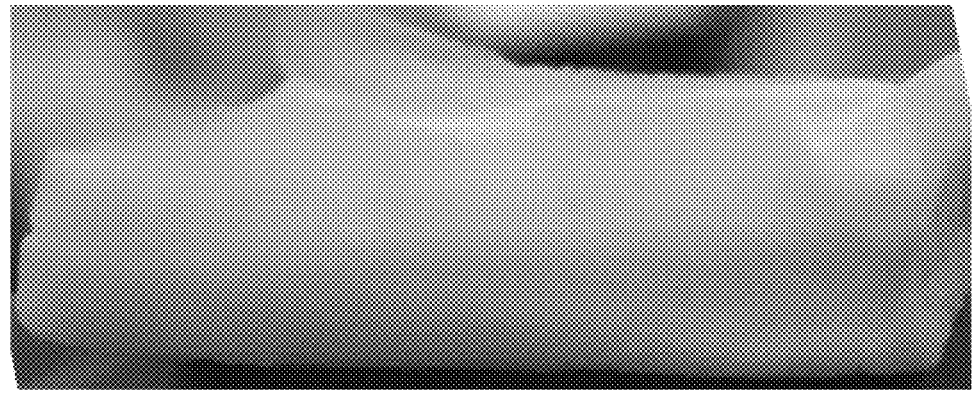
FIG. 3 represents another example multi-layered delivery device according to embodiments of the present invention. The pictured also features two layers: one lighter top layer containing 5-fluorouracil, a chemotherapeutic, and one darker bottom layer containing cisplatin, another chemotherapeutic.

After all the desired layers have been added, the combined solid is moved into a lyophilization chamber for about one to three days, depending on the number of devices loaded into the chamber. After the lyophilization removes all liquids, the multi-layer device is ready for use, as illustrated in the examples of FIG. 2 and FIG. 3.

In one representative embodiment, a multi-layered device may be used for the delivery of multiple agents over a concurrent period of time. For example, if use for the treatment and pain mitigation of mucositis is desired, one layer may include a pain mitigator, and one layer may include an agent for the treatment of mucositis.

Figure 4:
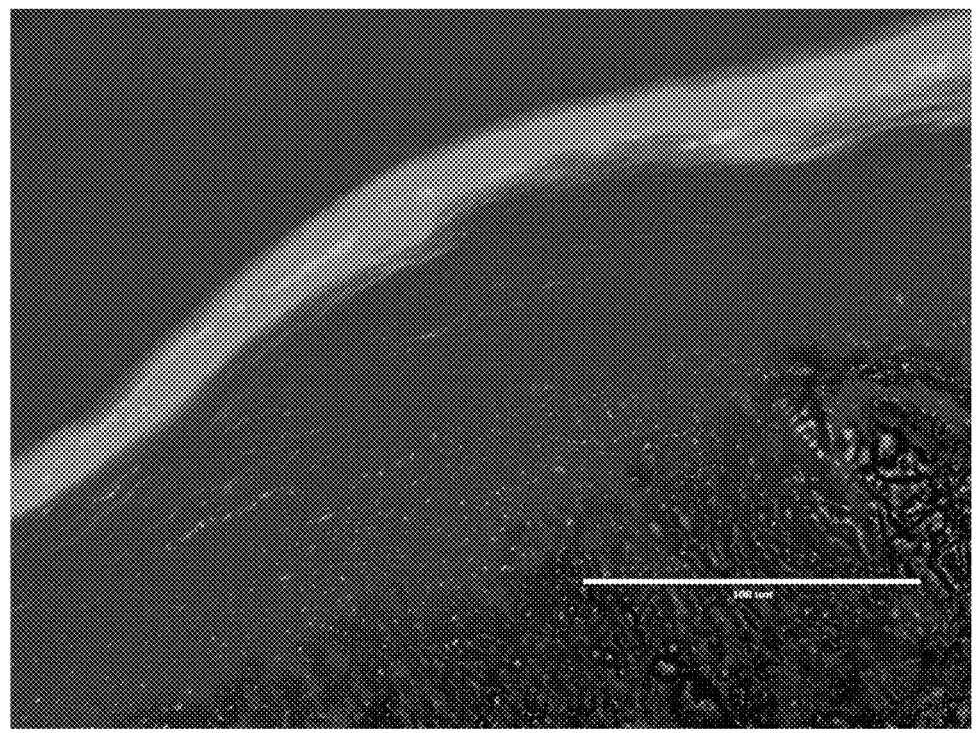
FIG. 4 is a microscope image taken from oral buccal tissue. The red light is from the Cy5 fluorescent dye and the green light is from the FITC fluorescent dye.
Figures 5A, 5B:
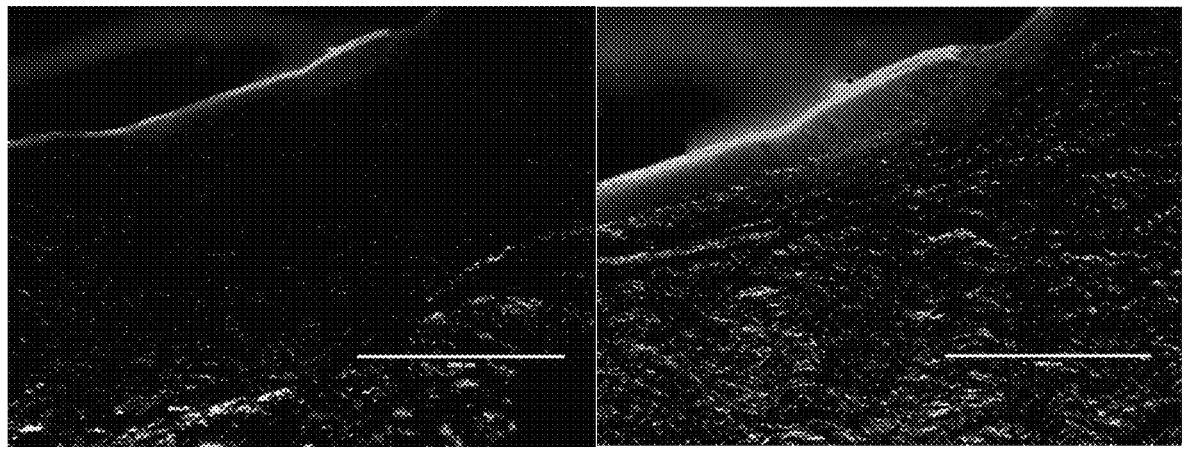
FIGS. 5A-5C show three images taken from lamb buccal tissue at different time points.
Figure 5C:
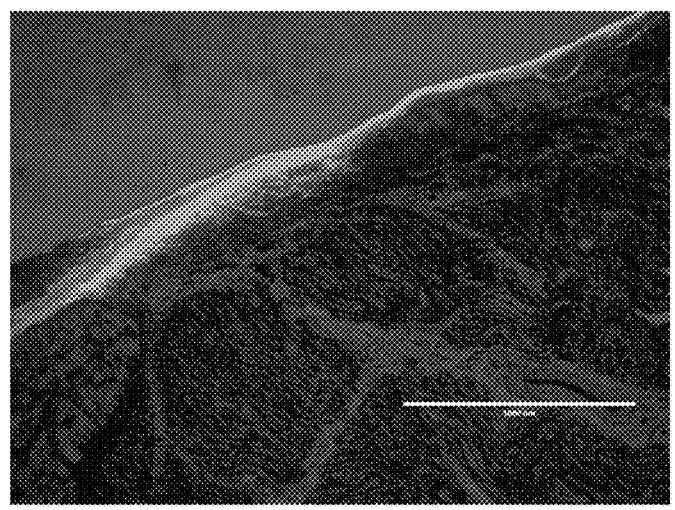

In another representative embodiment, a multi-layered device may be used for the delivery of multiple agents over a prolonged period of time (FIG. 4, FIG. 5). If the example of mucositis is again used, multiple layers may include a pain mitigator in free form, a pain mitigator encapsulated within particles and an agent for the treatment of mucositis encapsulated within particles. The initial freeform layer is able to provide immediate pain relief, and the subsequent particle-encapsulated layers are capable of delivering particles beneath the tissue, where they further release their agents over a period of days, providing longer-term pain relief and treatment. FIG. 4 and FIG. 5 illustrate this effect. Fluorescence was used in order to provide detection. As shown, the multiple fluorescent layers released over time and permeated the tissue at different rates, providing a customized treatment.

In another embodiment, each layer of the multi-layered device may include the same agent encapsulated within particles. This may prove useful in the treatment of topical conditions such as burns. The treatment device is able to be topically adhered to the site of a burn on the skin by means of a standard adhesive bandage. If use for a burn is desired, each layer may include an antibacterial agent or pain mitigator encapsulated within particles or otherwise. The device itself is then able to release the particles over time as each layer degrades.

In another embodiment, the device can also be customized depending on necessity. Psoriasis can be used as an example. Psoriasis is known to appear in flares which are long lasting. The delivery of an appropriate treatment agent such as allantoin encapsulated within the particles to the psoriasis location possesses the ability to provide significantly higher efficacy than periodic and uneven current topical treatment methods. These particles will deliver allantoin over time where it is needed. Likewise, agents such as allantoin can also be included in free form in a multitude of formulations to customize delivery. A combination of free allantoin in one layer and allantoin-encapsulating particles in another layer can be used to provide an initial bolus agent delivery and subsequent particle delivery which will provide longer term relief. In one embodiment, allantoin-encapsulating particles are included within one layer and free allantoin is included within another layer for this purpose. Multiple layers containing a free agent may also be used to provide longer delivery if particle encapsulation is not desired. Allantoin may be delivered over time as each layer degrades, with the second layers providing additional agent to the delivery site once the first layer has completed its delivery and degraded.

The embodiments of the described above are intended to be merely exemplary; numerous variations and modifications will be apparent to those skilled in the art. All such variations and modifications are intended to be within the scope of the present invention as defined in the appended claims.

REFERENCES

"Burns: Types, Treatments, and More." Healthline. N.p., n.d. Web. 28 Jun. 2016. www.healthline.com/health/burns#Overview1.

"What Is Melanoma Skin Cancer?" What Is Melanoma Skin Cancer? N.p., n.d. Web. 28 Jun. 2016. www.cancer.org/cancer/skincancer-melanoma/detailedguide/melanoma-skin-cancer-what-is-melanoma.

"The Oral Cancer Foundation." The Oral Cancer Foundation. Oral Cancer Foundation, n.d. Web. 27 Jun. 2016.

"First Aid: Burns." First Aid: Burns. N.p., n.d. Web. 28 Jun. 2016. familydoctor.org/familydoctor/en/prevention-wellness/staying-healthy/first-aid/first-aid-burns.html.

"Psoriasis Foundation." Psoriasis Foundation, n.d. Web. 28 Jun. 2016. www.psoriasis.org%2Fabout-psoriasis.

"Causes and Triggers." Psoriasis Causes and Known Triggers. N.p., n.d. Web. 29 Jun. 2016. www.psoriasis.org/about-psoriasis/causes.

"Skin Cancer Foundation." Melanoma. N.p., n.d. Web. 29 Jun. 2016. www.skincancer.org/skin-cancer-information/melanoma.

"Mucositis." Mucositis. Oral Cancer Foundation, n.d. Web. 21 Jan. 2016.

Weinberg M A, Estefan D J. "Assessing oral malignancies". AmFam Physician. 2002, 65 (7): 1379-1384

"The Oral Cancer Foundation." The Oral Cancer Foundation. Oral Cancer Foundation, n.d. Web. 21 Jan. 2016.

"Mucositis." Mucositis. Oral Cancer Foundation, n.d. Web. 21 Jan. 2016.

Gillenwater A, Papadimitrakopoulou, V, Richards-Kortum, R. "Oral Premalignancy: New Methods of Detection and Treatment". Curr Oncol Rep. 2006 March; 8(2): 146-154

Jacobson J J, Epstein J B, Eichmiller F C, Gibson T B, Carls G S, Vogtmann E, Wang S, Murphy B. "The cost burden of oral, oral pharyngeal, and salivary gland cancers in three groups: commercial insurance, Medicare, and Medicaid." Head and Neck Oncology 2012; 4:15. doi: 10.1186/1758-3284-4-15. Epub 2012 Apr. 26.

jco.ascopubs.org/content/26/29/4731.full

Barker, N. van de Wetering, M. Clevers H. "The intestinal stem cell". Genes & Dev 2008 22:1856-1864

Shaw, D. Gohil, K. Basson M. "Intestinal mucosal atrophy and adaptation" 2012 18(44): 6357-6375 www.medscape.com/viewarticle/820753

Hookman, Perry, and Jamie S. Barkin. "*Clostridium difficile* associated infection, diarrhea and colitis." World journal of gastroenterology: WJG 15.13 (2009): 1554.

www.chp.edu/~/media/chp/departments-and-services/pediatric-surgery/documents/enema-administration.ashx?la=en Youssef N N, Barksdale E J, Griffiths J M, Flores A F, Di Lorenzo C. "Management of Intractable Constipation With Antegrade Enemas in Neurologically Intact Children" Journal of Pediatric Gastroenterology & Nutrition. 2002 34(4): 402-405

Hanauer, S B, Robinson M, Pruitt R, Lazenby A J, Persson T, Nilsson G, Walton-Bowen K, Haskell L P, Levine J G. "Budesonide enema for the treatment of active, distal ulcerative colitis and proctitis: A dose-ranging study". Gastroenterology 115(3) 1998 525-532.

patient.info/doctor/prescribing-for-children

Murata Y, Sasaki N, Miyamoto E, Kawashima S. "Use of floating alginate gel beads for stomach-specific drug delivery". Eur J Pharm Biopharm. 2000 September; 50(2):221-6

Laksitorini M, Prasasty V D, Kiptoo P K, Siahaan T J. "Pathways and progress in improving drug delivery through the intestinal mucosa and blood-brain barriers." Ther Deliv. 2014 5(10):1143-63. doi: 10.4155/tde.14.67.

Lai, S. Wang, Y. Hanes J. "Mucus-penetrating nanoparticles for drug and gene delivery to mucosal tissues". Adv Drug Deliv Rev. 2009 Feb. 27; 61(2): 158-171

Bhandari, Bhesh. "Food Materials Science and Engineering" 2012 section 8.2: Nutrient Digestion and Absorption in the Gastrointestinal Tract www.livestrong.com/article/312184-the-three-phases-of-the-food-digestion-process/

Living with Anal Cancer—Causes & Risk Factors—the HPV and Anal cancer foundation web site.

Cancer of the Anus, Anal Canal, and Anorectum—fact sheet, Surveillance, Epidemiology, and End Result program (SEER), NIH.

Cancer of the Colon and Rectum—fact sheet, Surveillance, Epidemiology, and End Result program (SEER), NIH.

fightcolorectalcancer.org/fight-it/managing-side-effects/

Anatomy and Histology of the Small and Large Intestine-jpck.zju.edu.cn/jcyxjp/files/ge/05/MT/0511.pdf Clinical features, staging, and treatment of anal cancer—uptodate.com.

Clinical presentation, diagnosis, and staging of colorectal cancer—uptodate.com

Colorectal Cancer—Detailed guide, American Cancer Society. Cancer.org.

Glynne-Jones, R., et al. "Anal cancer: ESMO Clinical Practice Guidelines for diagnosis, treatment and follow-up." Annals of Oncology 21. suppl 5 (2010): v87-v92.

Living with Anal Cancer/Treatment for Anal Cancer, the HPV and Anal cancer foundation—website.

Paun, Bogdan C., et al. "Postoperative complications following surgery for rectal cancer." Annals of surgery 251.5 (2010): 807-818.

Koh P K, Tang C L, Eu K W, et al. A systematic review of the function and complications of colonic pouches. Int J Colorectal Dis. 2007; 22:543-548.

Adjuvant therapy for resected rectal adenocarcinoma—uptodate.com.

Gupta K C, Kumar R. Drug release behavior of beads and microgranules of chitosan. Biomaterials 2000; 21: 1115-1119.

Kulkarnia A R, Soppimatha K S, Aminabhavia T M, Rudzinskib W E. In-vitro release kinetics of cefadroxil-loaded sodium alginate interpenetrating network beads. European Journal of Pharmaceutics and Biopharmaceutics 2001; 51: 127-133.

Liu, Z. et al., Adv. Drug Deliv. Rev. 2008, 60, 1650-1662.

Bardot, P. M.; et al. Presses universitaires de Franche-Comté, mars 2009. 308, ISBN: 2-84867-249-8.

Patil, Poonam, Daksha Chavanke, and Milind Wagh. "A review on ionotropic gelation method: novel approach for controlled gastroretentive gelispheres." Int J Pharm Pharm Sci 4.4 (2012): 27-32.

Zhang, Zheng, et al. "Polymeric nanoparticles-based topical delivery devices for the treatment of dermatological diseases." Wiley Interdisciplinary Reviews: Nanomedicine and Nanobiotechnology 5.3 (2013): 205-218.

Zhang, Hong, et al. "Monodisperse chitosan nanoparticles for mucosal drug delivery." Biomacromolecules 5.6 (2004): 2461-2468.

[21] Nagpal, Kalpana, Shailendra Kumar Singh, and Dina Nath Mishra. "Chitosan nanoparticles: a promising device in novel drug delivery." Chemical and Pharmaceutical Bulletin 58.11 (2010): 1423-1430.

What is claimed is:

1. A device for delivery of a first therapeutic agent and a second therapeutic agent to a site in epithelial tissue, the device comprising:
    a first layer comprising:
        a first porous, mucoadhesive, freeze-dried polymeric matrix having first and second opposed surfaces, the first matrix formed by a composition comprising chitosan, a hydration promoter, a particle adhesion inhibitor comprising hydroxypropylmethylcellulose (HPMC), a particle aggregation inhibitor in a concentration from 1% to 10% by weight of the first layer, and a free amount of the first therapeutic agent,
        wherein the hydration promoter is selected from the group consisting of ethylene glycol, propylene glycol, beta-propylene glycol, and combinations thereof,
        wherein the particle aggregation inhibitor is sucralose, and
        a plurality of first particles embedded within the first matrix so as to be directly surrounded by, and in contact with, the first matrix, the first particles encapsulating the first therapeutic agent and comprising chitosan so as to provide controlled release of the first therapeutic agent from the first particles through one of the opposed surfaces of the first matrix, wherein the average diameter of the plurality of first particles is from about 500 nm to about 2000 nm; the first particles further comprising sodium tripolyphosphate, and
    a second layer, adjacent to the first layer, the second layer comprising:
        a second, freeze-dried polymeric matrix having third and fourth opposed surfaces, the second matrix formed by a composition comprising chitosan and a plurality of second particles embedded within the second matrix, wherein the second particles comprise the second therapeutic agent,
        wherein the first surface of the first layer is configured to be attached to the site in the epithelial tissue,
        wherein the second surface of the first layer is attached to the third surface of the second layer,
        wherein the fourth surface of the second layer is covered with a covering selected from the group consisting of a film, a layer, and a membrane, the covering being configured to restrict passage of any therapeutic agent through the fourth surface of the second layer while still being water permeable, and
        wherein at least one of the first therapeutic agent and second therapeutic agent is cisplatin.

2. A device according to claim 1, wherein the second particles comprise positively charged chitosan.

3. A device according to claim 1, wherein one or both of the opposed surfaces of the first matrix is permeable to water.

4. A device according to claim 1, wherein one or both of the opposed surfaces of the second matrix is permeable to water.

5. A device according to claim 1, wherein the first therapeutic agent and the second therapeutic agent are the same therapeutic agent.

6. A device according to claim 1, wherein the first particles are made from pure chitosan.

7. A device according to claim 1, wherein a layer selected from the group consisting of the first layer, the second layer, and combinations thereof, includes a pain mitigator, wherein the pain mitigator is present in a form selected from the group consisting of free, encapsulated, and combinations thereof.

* * * * *